US009220441B2

(12) United States Patent
Yoo et al.

(10) Patent No.: US 9,220,441 B2
(45) Date of Patent: Dec. 29, 2015

(54) MEDICAL SYSTEM AND METHOD FOR PROVIDING MEASUREMENT INFORMATION USING THREE-DIMENSIONAL CALIPER

(71) Applicant: SAMSUNG MEDISON CO., LTD., Hongcheon-gun, Gangwon-do (KR)

(72) Inventors: Jun-sang Yoo, Gangwon-do (KR); Sung-yoon Kim, Gangwon-do (KR); Han-jun Kim, Gangwon-do (KR); Jun-kyo Lee, Gangwon-do (KR)

(73) Assignee: SAMSUNG MEDISON CO., LTD., Hongcheon-Gun, Gangwon-Do (KR)

( * ) Notice: Subject to any disclaimer, the term of this patent is extended or adjusted under 35 U.S.C. 154(b) by 65 days.

(21) Appl. No.: 14/095,692

(22) Filed: Dec. 3, 2013

(65) Prior Publication Data

US 2014/0152654 A1    Jun. 5, 2014

(30) Foreign Application Priority Data

Dec. 4, 2012  (KR) .......................... 10-2012-0139469

(51) Int. Cl.
*G06T 15/00* (2011.01)
*A61B 5/107* (2006.01)
(Continued)

(52) U.S. Cl.
CPC ............... *A61B 5/107* (2013.01); *A61B 5/1072* (2013.01); *A61B 8/465* (2013.01); *A61B 8/469* (2013.01); *A61B 8/483* (2013.01); *G01S 7/52063* (2013.01);
(Continued)

(58) Field of Classification Search
CPC ........ A61B 8/465; A61B 8/469; A61B 8/483; A61B 5/107; A61B 5/1072; G01S 15/8993; G01S 7/52063; G06T 2207/20104; G06T 2207/30004; G06T 7/0081
USPC .................. 345/419; 382/128; 600/443, 547; 606/41; 73/632
See application file for complete search history.

(56) References Cited

U.S. PATENT DOCUMENTS 6,298,726 B1 * 10/2001 Adachi et al. ................... 73/632
6,832,111 B2 * 12/2004 Tu et al. ......................... 600/547
(Continued)

FOREIGN PATENT DOCUMENTS

EP   2302414 A2    3/2011
JP   11299787 A   11/1999
(Continued)

OTHER PUBLICATIONS

European Search Report issued in European Applicatin No. 13194369.8-1812 dated Mar. 17, 2014.
(Continued)

*Primary Examiner* — Phu K Nguyen
(74) *Attorney, Agent, or Firm* — McDermott Will & Emery LLP

(57) ABSTRACT

Provided are a medical system and a method for providing measurement information by setting a three-dimensional (3D) caliper on a 3D image. The medical system includes: an image data acquisition unit that acquires image data corresponding to a 3D image of a living body including an object; a user input unit that receives user input information; and a processor that generates 3D data by using the image data and the 3D image by using the 3D data, detects 3D geometry information corresponding to a 3D caliper from the 3D data based on the user input information, sets the 3D caliper on the 3D image based on the detected 3D geometry information, and creates measurement information.

12 Claims, 10 Drawing Sheets

(51) Int. Cl.
*A61B 8/00* (2006.01)
*A61B 8/08* (2006.01)
*G01S 15/89* (2006.01)
*G01S 7/52* (2006.01)
*G06T 7/00* (2006.01)

(52) U.S. Cl.
CPC ......... *G01S 7/52073* (2013.01); *G01S 15/8993* (2013.01); *G06T 7/0081* (2013.01); *G06T 2207/10136* (2013.01); *G06T 2207/20104* (2013.01); *G06T 2207/30004* (2013.01)

(56) References Cited

U.S. PATENT DOCUMENTS 7,419,487 B2 * 9/2008 Johnson et al. ............. 606/41
8,715,189 B2 * 5/2014 Kanayama et al. ........... 600/443
8,831,311 B2 * 9/2014 Swamy et al. ................ 382/128
2011/0018429 A1 1/2011 Spindler et al.
2011/0172531 A1 7/2011 Kanayama et al.
2012/0176365 A1 7/2012 Hansegard et al.

FOREIGN PATENT DOCUMENTS

KR 10-2011-0059923 A 6/2011
KR 10-2011-0087355 A 8/2011
WO 2007023459 A2 3/2007

OTHER PUBLICATIONS

Korean Office Action issued in Korean Application No. 10-2012-0139469 dated Jan. 29, 2014. w/English translation.

* cited by examiner

MEDICAL SYSTEM AND METHOD FOR PROVIDING MEASUREMENT INFORMATION USING THREE-DIMENSIONAL CALIPER

RELATED APPLICATIONS

This application claims the benefit of Korean Patent Application No. 10-2012-0139469, filed on Dec. 4, 2012, in the Korean Intellectual Property Office, the disclosure of which is incorporated herein in its entirety by reference.

BACKGROUND

1. Field

One or more embodiments of the present invention relate to a medical system, and more particularly, to a medical system and method for providing measurement information by using a three-dimensional (3D) caliper.

2. Description of the Related Art

Medical systems provide images of living bodies, and have been used in a wide range of fields. Examples of the medical systems may include a magnetic resonance imaging (MRI) system, a computed tomography (CT) system, a positron emission tomography (PET)-CT (PET-CT) system, and an ultrasound system. Hereinafter, for convenience of explanation, an ultrasound system for providing images of living bodies is described as an example of the medical system.

Due to its non-invasive and non-destructive nature, an ultrasound system has been widely used in the medical field that requires information about the inside of living bodies. The ultrasound system also plays a critical role in the medical profession since it can provide real-time, high-resolution images of tissue of a living body to a doctor without the need for a surgical procedure that directly incises the living body for observation.

The ultrasound system provides a 3D ultrasound image including spatial information and clinical information such as anatomical information, which cannot be provided by a two-dimensional (2D) ultrasound image. In detail, the ultrasound system continuously transmits ultrasound signals to a living body and receives ultrasound echo signals reflected from the living body to produce 3D data (i.e., volume data), and performs volume rendering on the volume data to create the 3D ultrasound image.

To provide measurement information, The ultrasound system also sets a caliper in an ultrasound image and measures a size (distance, perimeter, area, volume, etc.) of an object within a living body by using the set caliper Conventionally, to measure a size of an object in a 3D ultrasound image, a 2D caliper is set in a cross-sectional image corresponding to the 3D ultrasound image to produce measurement information. Thus, there is a need for a system for providing measurement information by setting a 3D caliper in a 3D ultrasound image.

SUMMARY

One or more embodiments of the present invention include a medical system and method for providing measurement information by using a three-dimensional (3D) caliper that is set in a 3D image.

Additional aspects will be set forth in part in the description which follows and, in part, will be apparent from the description, or may be learned by practice of the presented embodiments.

According to one or more embodiments of the present invention, a medical system includes: an image data acquisition unit that acquires image data corresponding to a three-dimensional (3D) image of a living body including an object; a user input unit that receives user input information; and a processor that generates 3D data by using the image data and the 3D image by using the 3D data, detects 3D geometry information corresponding to a 3D caliper from the 3D data based on the user input information, sets the 3D caliper on the 3D image based on the detected 3D geometry information, and creates measurement information.

According to one or more embodiments of the present invention, a method of providing measurement information includes: acquiring image data corresponding to a three-dimensional (3D) image of a living body including an object; creating 3D data by using the image data; creating the 3D image by using the 3D data; receiving user input information; detecting 3D geometry information corresponding to a 3D caliper from the 3D data based on the user input information; and setting the 3D caliper on the 3D image based on the detected 3D geometry information to create measurement information.

The method and system for providing measurement information by using a 3D caliper according to the embodiments of the present invention may enable direct setting of the 3D caliper on a 3D image without using a 2D image, thereby increasing user's convenience.

The method and system may provide measurement information for a 3D image by using a plane at an arbitrary position, thereby easily providing 2-D and 3-D position information of an object for a user.

BRIEF DESCRIPTION OF THE DRAWINGS

These and/or other aspects will become apparent and more readily appreciated from the following description of the embodiments, taken in conjunction with the accompanying drawings of which.

DETAILED DESCRIPTION

Hereinafter, medical systems and methods for providing measurement information by using a three-dimensional (3D) caliper according to embodiments of the present invention will be described below with reference to the accompanying drawings. For convenience of explanation, an ultrasound system is described as the medical system. However, the medical system is not limited thereto, and may include a magnetic resonance imaging (MRI) system, a computed tomography (CT) system, a positron emission tomography (PET)-CT (PET-CT) system. Expressions such as "at least one of," when preceding a list of elements, modify the entire list of elements and do not modify the individual elements of the list.

Embodiment 1

Figure 1:
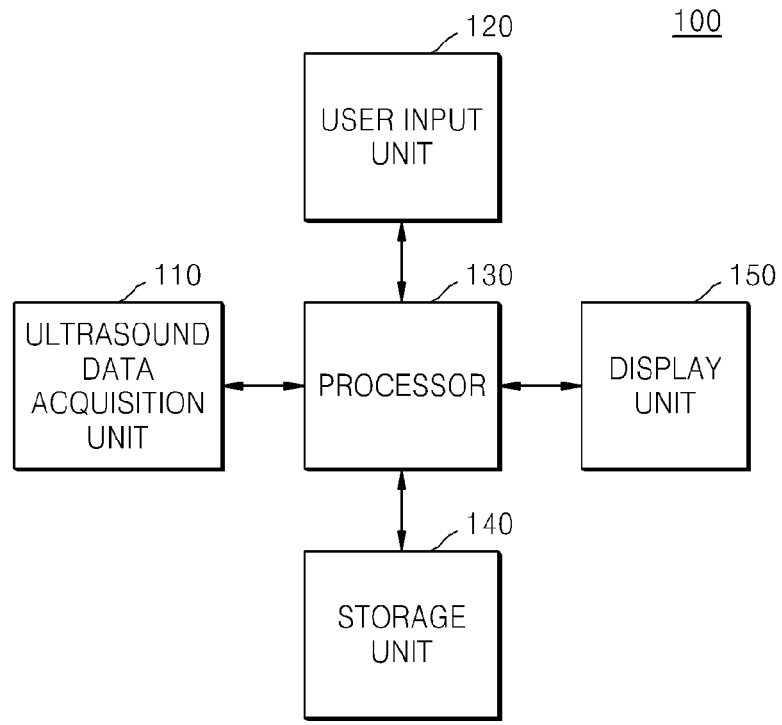
FIG. 1 is a block diagram showing a configuration of an ultrasound system according to an exemplary embodiment of the present invention.

FIG. 1 is a block diagram showing a configuration of an ultrasound system 100 according to an exemplary diagram of the present invention. Referring to FIG. 1, the ultrasound system 100 according to the present embodiment includes an ultrasound data acquisition unit 110, a user input unit 120, a processor 130, a storage unit 140, and a display unit 150.

The ultrasound data acquisition unit 110 acquires ultrasound data corresponding to an ultrasound image of a living body including an object such as blood vessels, the heart, the liver, and bones. The ultrasound data includes radio frequency (RF) data, but is not limited thereto.

Figure 2:
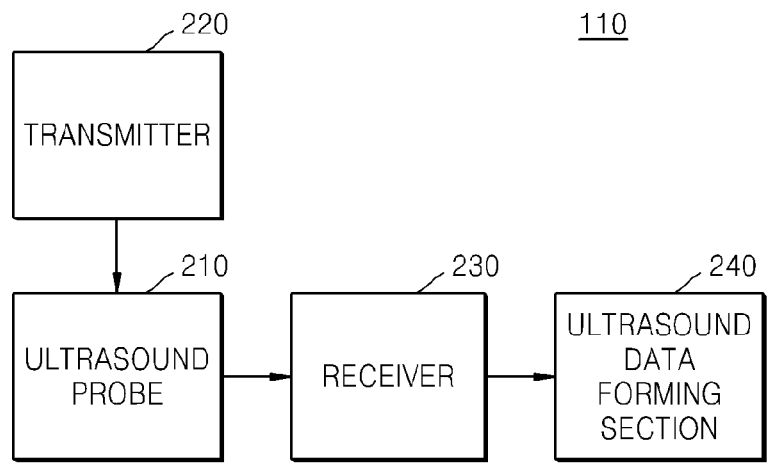
FIG. 2 is a block diagram showing a configuration of an ultrasound data acquisition unit in the ultrasound system of FIG. 1.

FIG. 2 is a block diagram showing a configuration of the ultrasound data acquisition unit 110. Referring to FIG. 2, the ultrasound data acquisition unit 110 includes an ultrasound probe 210, a transmitter 220, a receiver 230, and an ultrasound data forming section 240.

The ultrasound probe 210 includes a plurality of transducer elements (not shown) that convert electrical signals into ultrasound signals, and vice versa. The ultrasound probe 210 is configured to transmit an ultrasound signal to a living body and receive an ultrasound echo signal reflected from the living body to generate an electrical signal (hereinafter referred to as a "reception signal"). The reception signal is an analog signal. The ultrasound probe 210 includes a 3D probe and a two-dimensional (2D) array probe.

Figure 3:
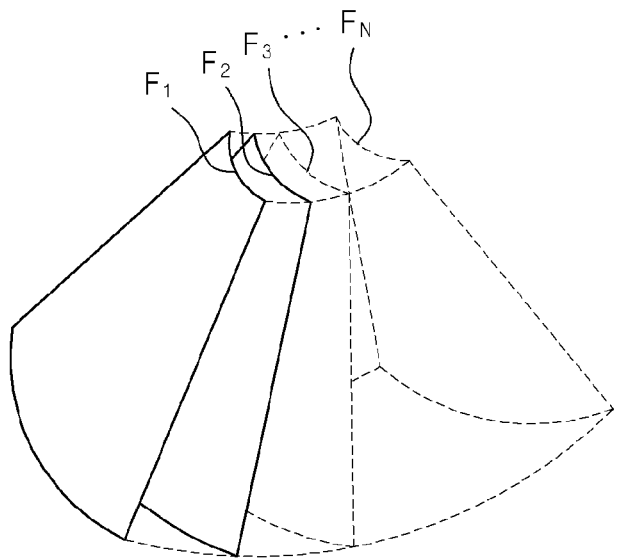
FIG. 3 is an exemplary diagram of a plurality of frames.

The transmitter 220 controls the transmission of an ultrasound signal. The transmitter 220 also produces an electrical signal (hereinafter referred to as a "transmission signal") that is used to obtain an ultrasound image in consideration of the transducer elements. In the present embodiment, the transmitter 220 creates a transmission signal that is used to obtain each of a plurality of frames Fi ($1 \leq i \leq N$) as shown in FIG. 3, in consideration of the transducer elements. Thus, upon receipt of the transmission signal from the transmitter 220, the ultrasound probe 210 converts the transmission signal into an ultrasound signal, transmits the ultrasound signal to a living body, and creates a reception signal based on an ultrasound echo signal reflected from the living body.

The receiver 230 performs analog-to-digital conversion on the reception signal provided by the ultrasound probe 210 to produce a digital signal. The receiver 230 also performs reception beamforming on the digital signal in consideration of positions of the transducer elements to create a focused reception signal. Since the reception beamforming may be performed by using various known methods, a detailed description thereof is omitted here.

The ultrasound data forming section 240 creates ultrasound data corresponding to an ultrasound image by using the focused reception signal provided by the receiver 230. According to the present embodiment, the ultrasound data forming section 240 forms ultrasound data corresponding to each of the plurality of frames Fi by using focused reception signals sequentially received from the receiver 230. The ultrasound data forming section 240 may also perform various signal processings, such as gain control, needed to form ultrasound data, on the focused reception signal.

Although the ultrasound data acquisition unit 110 has been described to transmit an ultrasound signal to a living body and receives an ultrasound echo signal reflected from the living body to acquire ultrasound data corresponding to an ultrasound image, the ultrasound data acquisition unit 110 may acquire ultrasound data from an external or internal device (not shown) connected to the ultrasound system 100 in a wired or wireless manner.

Referring back to FIG. 1, the user input unit 120 receives user input information. The input information includes first input information needed for setting a region of interest (ROI) corresponding to a 3D caliper on a 3D ultrasound image. The first input information contains 2D coordinates of the ROI on the 3D ultrasound image that is displayed on the display unit 150. The ROI includes a point, but is not limited thereto. The input information also includes second input information needed for selecting at least one of a plurality of objects within a living body. The input information further includes third input information needed for setting a reference value that will be used to determine a position of a 3D caliper (i.e., an ROI) with respect to a 3D ultrasound image in a depth direction. However, the input information is not limited thereto. The user input unit 120 includes a control panel, a track ball, a touch screen, a keyboard, and a mouse.

The processor 130 is connected to the ultrasound data acquisition unit 110 and the user input unit 120. The processor 130 includes a central processing unit (CPU), a microprocessor, and a graphic processing unit (GPU).

Figure 4:
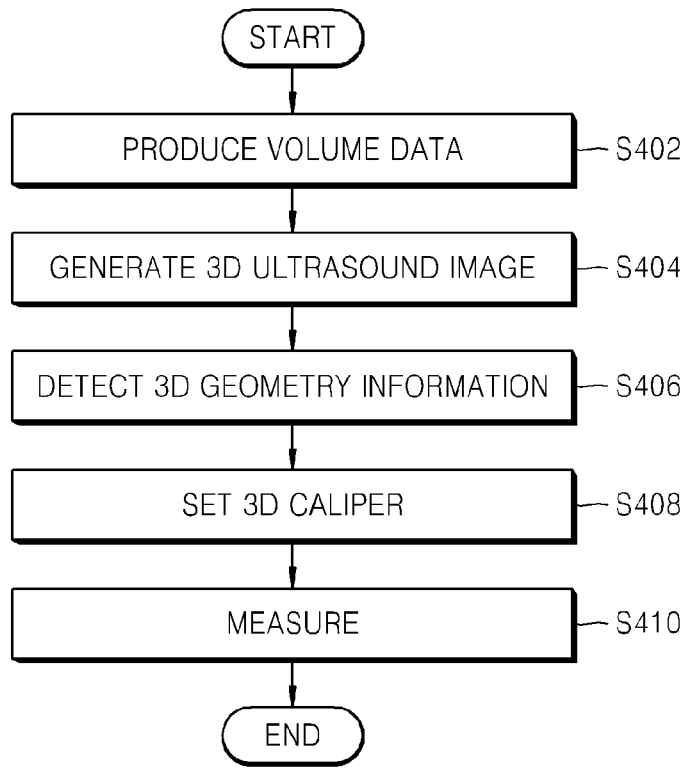
FIG. 4 is a flowchart of a method of creating measurement information by setting a three-dimensional (3D) caliper according to an exemplary embodiment of the present invention.
Figure 5:
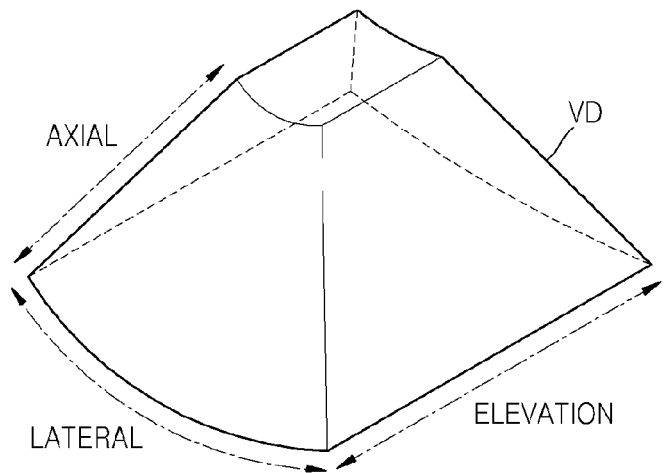
FIG. 5 is an exemplary diagram of volume data.

FIG. 4 is a flowchart illustrating a method of creating measurement information by setting a three-dimensional (3D) caliper, according to an exemplary embodiment of the present invention. Referring to FIGS. 1 and 4, the processor 130 produces volume data VD as shown in FIG. 5 by using ultrasound data provided by the ultrasound data acquisition unit 110 (S402).

The volume data VD consists of a plurality of frames Fi ($1 \leq i \leq N$) and includes a plurality of voxels having brightness values. Each of the plurality of voxels has 3D geometry information (i.e., 3D coordinates) for the volume data VD. In FIG. 5, an axial direction denotes the direction of propagation of an ultrasound signal with respect to transducer elements of the ultrasound probe 210. A lateral direction is a direction in which a scanline moves. An elevation direction is a scan direction of a frame (i.e., scanning plane), i.e., a depth direction of a 3D ultrasound image.

The processor 130 then performs volume rendering on the volume data VD to generate a 3D ultrasound image (S404). The 3D ultrasound image contains 3D geometry information. The volume rendering may include ray-casting, perspective rendering, and stereo rendering, but is not limited thereto. The 3D ultrasound image may be displayed on the display unit 150. Thus, a user may set an ROI corresponding to a 3D caliper on the 3D ultrasound image displayed on the display unit 150 by using the user input unit 120.

Figure 6:
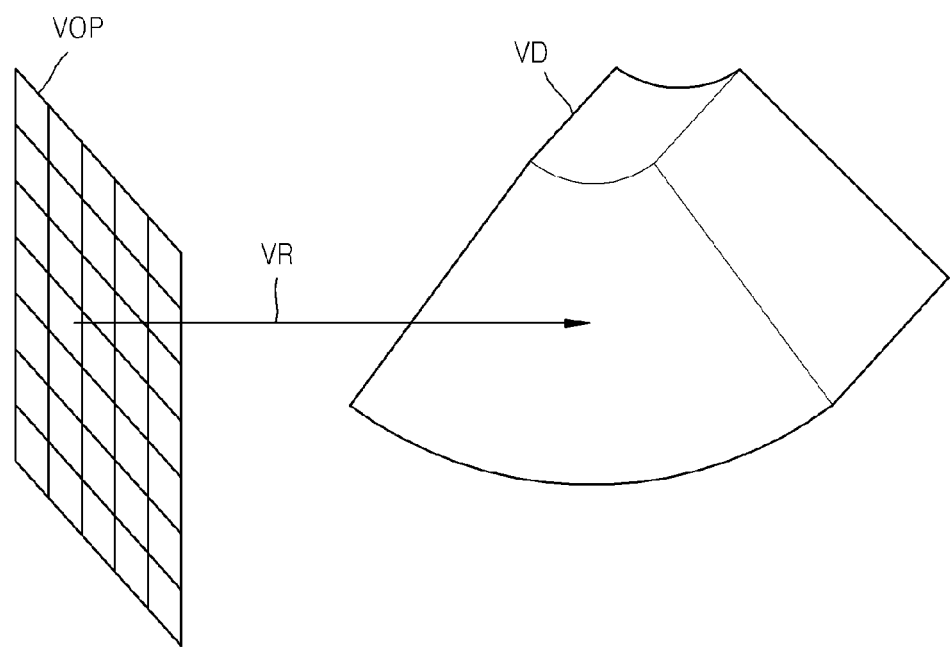
FIG. 6 is an exemplary diagram illustrating volume rendering.
Figure 7:
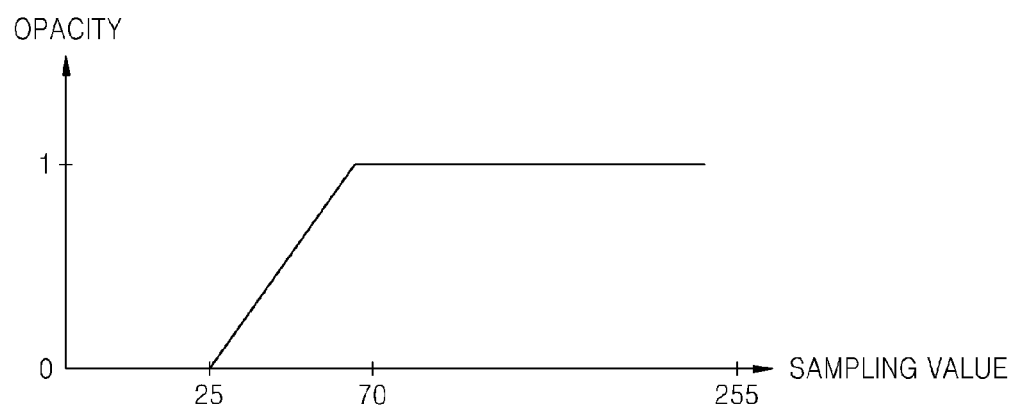
FIG. 7 is an exemplary diagram illustrating an opacity transfer function.

For example, as shown in FIG. 6, the processor 130 may set a virtual observation plane (VOP) including a plurality of pixels based on the volume data VD. The virtual observation plane VOP is a screen of the display unit 150 on which the 3D ultrasound image is displayed. The processor 130 projects a virtual ray VR from each of the plurality of pixels in the virtual observation plane VOP onto the volume data VD. The processor 130 then samples the virtual ray VR at sampling intervals and obtains sampling points and sampling values at the sampling points. Sampling values range from 0 through 255, but are not limited thereto. The processor 130 calculates opacity at a current sampling point by using an opacity transfer function. The opacity transfer function maps sampling values to opacity values. As shown in FIG. 7, a sampling value between 0 and 25 corresponds to an opacity value of 0. A sampling value between 25 and 75 linearly corresponds to an opacity value between 0 and 1. A sampling value between 70 and 255 corresponds to an opacity value of 1. The processor 130 calculates a pixel value corresponding to each of the pixels in the virtual observation plane VOP based on the sampling values and the corresponding opacity values.

Next, the processor detects 3D geometry information (i.e., 3D coordinates) of an ROI from the volume data VD (i.e., 3D ultrasound image) (S406).

Figure 8:
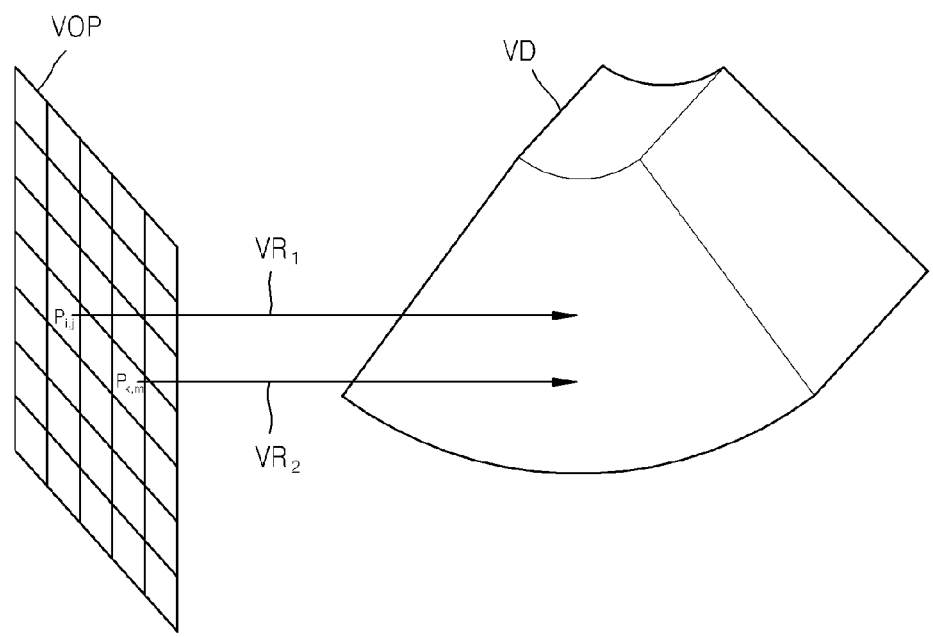
FIG. 8 is a diagram illustrating an observation plane, a region of interest (ROI), and a virtual ray according to an exemplary embodiment of the present invention.

In one embodiment, the processor 130 may set a reference value corresponding to an object according to a reference value preset for the object, based on input information (i.e., second input information) provided by the user input unit 120. The preset reference value may be stored in the storage unit 140. As shown in FIG. 6, the processor 130 sets a virtual observation plane VOP consisting of a plurality of pixels based on the volume data VD. The processor 130 detects pixels corresponding to an ROI (i.e., points) from the virtual observation plane VOP based on input information (i.e., first input information) provided by the user input unit 120. That is, as shown in FIG. 8, the processor 130 detects pixels $P_{i,j}$ and $P_{k,m}$ corresponding to the ROI based on 2D position information (i.e., 2D coordinates) of the ROI. The processor 130 then projects virtual rays $VR_1$ and $VR_2$ from the detected pixels $P_{i,j}$ and $P_{k,m}$ onto the volume data VD. The processor 130 also samples the virtual rays $VR_1$ and $VR_2$ at preset sampling intervals and acquires sampling points and sampling values at the sampling points. The processor 130 then detects a voxel corresponding to the reference value from the volume data VD based on the sampling value. In one embodiment, the processor 130 may cumulatively add sampling values along the propagation direction of the virtual rays $VR_1$ and $VR_2$ and detect a first voxel where a cumulative sum of the sampling values is greater than or equal to the reference value as the voxel corresponding to the reference value. In another embodiment, the processor 130 may compare a sampling value with a preset threshold value, detect sampling values that are greater than or equal to the preset threshold value, cumulatively add the detected sampling values along the propagation direction of the virtual rays $VR_1$ and $VR_2$, and detect a first voxel where a cumulative sum of the sampling values is greater than or equal to the reference value as the voxel corresponding to the reference value. In yet another embodiment, the processor 130 may compare a sampling value with a reference value, detect a first sampling value that is greater than or equal to the reference value, and detect a voxel corresponding to the first sampling value as the voxel corresponding to the reference value. The processor 130 then sets 3D geometry information (i.e., 3D coordinates) of the detected voxel as 3D geometry information (i.e., 3D coordinates) of an ROI (i.e., a 3D caliper). In still another embodiment, the processor 130 sets a reference value corresponding to the object based on input information (i.e., second input information and third input information) provided by the user input unit 120, and detects 3D geometry information of an ROI based on the set reference value.

Then, the processor 130 sets a 3D caliper on the 3D ultrasound image based on the detected 3D geometry information (i.e., 3D coordinates) (S408), and performs measurement based on the set 3D caliper to create measurement information (S410). Since the measurement with a caliper may be performed by using various known methods, a detailed description thereof is omitted here.

The processor 130 may selectively set a 3D caliper by using stereo rendering. That is, the processor 130 may project at least two virtual rays having different angles from each of the pixels corresponding to the ROI onto the volume data VD.

In addition, the processor 130 may selectively detect 3D geometry information corresponding to the 3D caliper by using perspective ray casting. Since the perspective ray casting may be performed by using various known methods, a detailed description thereof is omitted here.

Referring back to FIG. 1, the storage unit 140 stores ultrasound data acquired by the ultrasound data acquisition unit 110 as well as input information received from the user input unit 120. In addition, the storage unit 140 may store volume data VD created by the processor 130 and preset reference values.

The display unit 150 displays 3D ultrasound images and measurement information generated by the processor 130 as well as 3D calipers.

Embodiment 2

Figure 9:
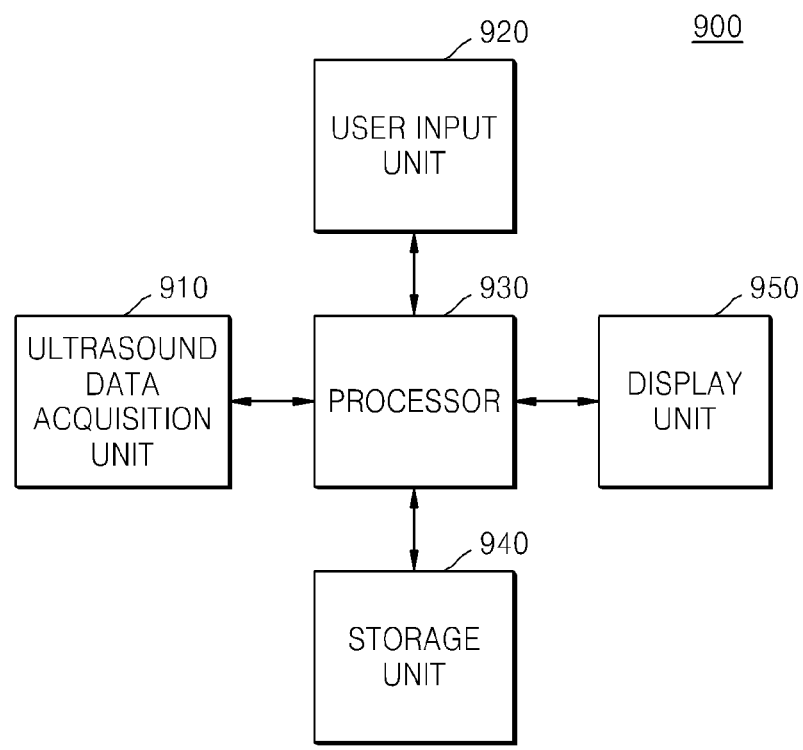
FIG. 9 is a block diagram showing a configuration of an ultrasound system according to another exemplary embodiment of the present invention.

FIG. 9 is a block diagram showing a configuration of an ultrasound system 900 according to another exemplary embodiment of the present invention. Referring to FIG. 9, the ultrasound system 900 according to the present embodiment includes an ultrasound data acquisition unit 910, a user input unit 920, a processor 930, a storage unit 940, and a display unit 950.

The ultrasound data acquisition unit 910 acquires ultrasound data corresponding to an ultrasound image of a living body. Since the ultrasound data acquisition unit 910 has substantially the same function and construction as the ultrasound data acquisition unit 110, a detailed description thereof is omitted here.

The user input unit 920 receives user input information. In the present embodiment, the input information includes first input information needed for setting a virtual plane on a 3D ultrasound image and second input information needed for changing a 3D position of the virtual plane. The second input information contains at least one of information needed for rotating the virtual plane and information needed for moving the virtual plane. The input information further includes third input information needed for setting an ROI corresponding to a 3D caliper. The third input information contains 2D position information (coordinates) of the ROI on a 3D ultrasound image. The user input unit 920 includes a control panel, a track ball, a touch screen, a keyboard, and a mouse.

The processor 930 is connected to the ultrasound data acquisition unit 910 and the user input unit 920. The processor 930 includes a CPU, a microprocessor, and a GPU.

Figure 10:
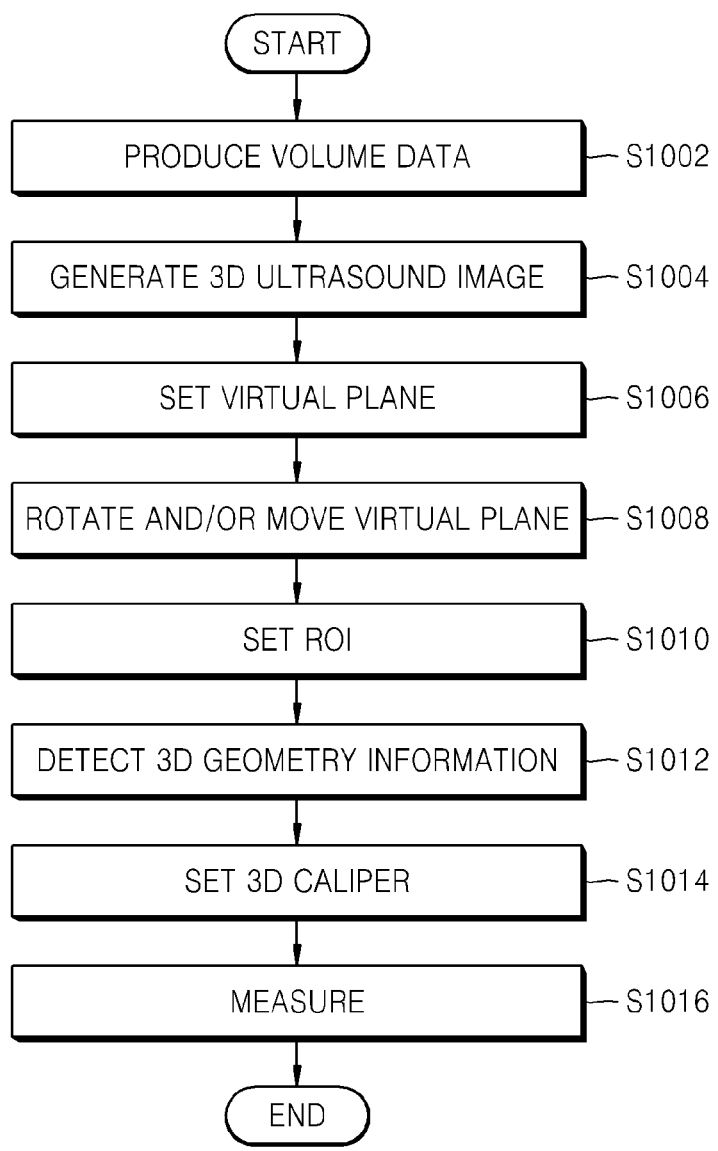
FIG. 10 is a flowchart of a method of creating measurement information by setting a 3D caliper according to another exemplary embodiment of the present invention.

FIG. 10 is a flowchart of a method of creating measurement information by setting a 3D caliper according to another exemplary embodiment of the present invention. Referring to FIGS. 9 and 10, the processor 930 produces volume data VD as shown in FIG. 5 by using ultrasound data provided by the ultrasound data acquisition unit 910 (S1002).

The processor 930 performs volume rendering on the volume data VD to generate a 3D ultrasound image (S1004). In the present embodiment, the volume rendering includes perspective rendering.

Figure 11:
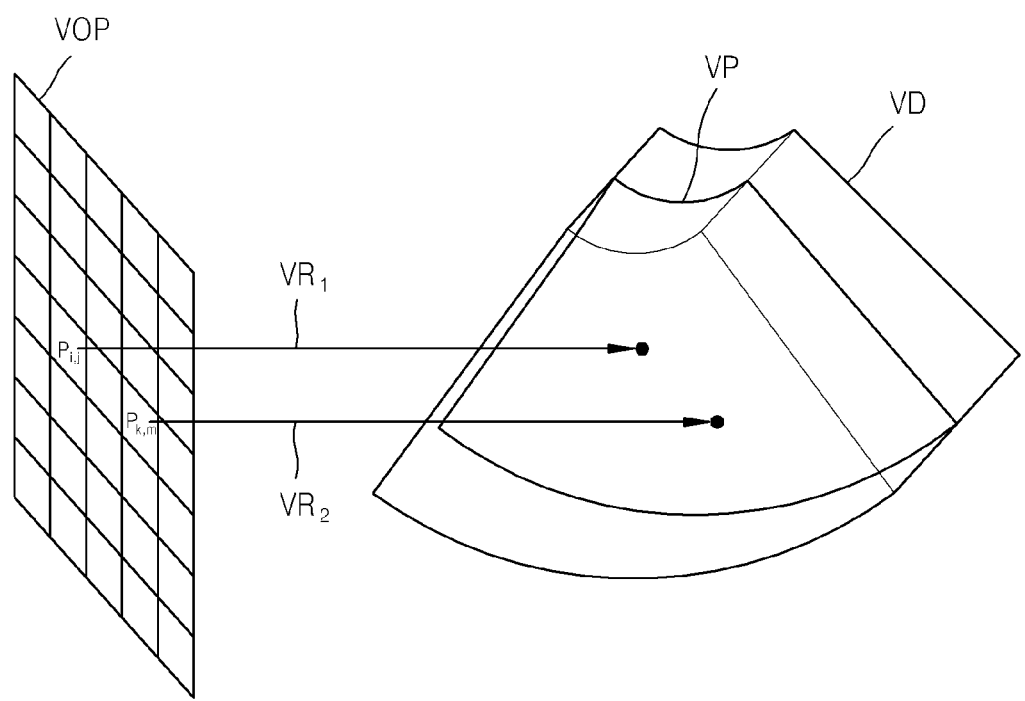
FIG. 11 is a diagram of a virtual plane according to another exemplary embodiment of the present invention.

The processor 930 then sets a virtual plane based on input information provided by the user input unit 920 (S1006). In the present embodiment, as shown in FIG. 11, the processor 930 sets a virtual plane (VP) based on input information (i.e., first input information) provided by the user input unit 920. In FIG. 11, VOP denotes a virtual observation plane . . . .

The processor 930 then changes a 3D position of the virtual plane VP based on input information provided by the user input unit 920 and places the virtual plane VP at a predetermined position of the volume data VD (S1008). In the present embodiment, the processor 930 performs at least one of rotation and movement of the virtual plane (VP) based on the second input information provided by the user input unit 920.

Next, the processor 930 sets an ROI on the 3D ultrasound image displayed on the display unit 950 based on the third input information provided by the user input unit 920 (S1010).

The processor 930 then detects 3D geometry information (i.e., 3D coordinates) of the ROI from the volume data VD in which the virtual plane VP has been set (S1012). In the present embodiment, as shown in FIG. 11, the processor 930 sets a virtual observation plane VOP including a plurality of pixels based on the volume data VD. The processor 930 detects pixels corresponding to an ROI (i.e., points) from the virtual observation plane VOP. That is, as shown in FIG. 11, the processor 930 detects pixels $P_{i,j}$ and $P_{k,m}$ corresponding to the ROI based on 2D position information (i.e., 2D coordinates) of the ROI. The processor 930 then projects virtual rays $VR_1$ and $VR_2$ from the detected pixels $P_{i,j}$ and $P_{k,m}$ onto the volume data VD and detects a voxel at which the virtual rays $VR_1$ and $VR_2$ and the virtual plane VP meet each other. The processor 930 sets 3D geometry information (i.e., 3D coordinates) of the detected voxel as 3D geometry information (i.e., 3D coordinates) of the ROI (i.e., 3D caliper).

Next, the processor 930 sets a 3D caliper on the virtual plane VP based on the detected 3D geometry information (i.e., 3D coordinates) (S1014). In detail, the processor 930 sets a virtual plane VP on the 3D ultrasound image based on the first input information and then sets a 2D caliper having depth information in a depth direction of the 3D ultrasound image on the virtual plane VP as a 3D caliper, based on the detected 3D geometry information (i.e., 3D coordinates).

The processor 930 then performs measurement based on the set 3D caliper to create measurement information (S1016). That is, the processor 930 measures a length of the object by using the 2D caliper to create length information as well as measurement information including the length information and the depth information.

The processor 930 may selectively create an ultrasound image (i.e., cross-sectional image) corresponding to the virtual plane by using the volume data VD, set an ROI on the cross-sectional image based on the third input information provided by the user input unit 920, and perform measurement based on the set ROI to create measurement information.

Referring back to FIG. 9, the storage unit 940 stores ultrasound data acquired by the ultrasound data acquisition unit 910 as well as input information received from the user input unit 920. In addition, the storage unit 940 may store volume data VD created by the processor 930.

The display unit 950 displays 3D ultrasound images and measurement information generated by the processor 930 as well as 3D calipers. In addition, the display unit 950 displays a cross-sectional image generated by the processor 930.

Embodiment 3

Figure 12:
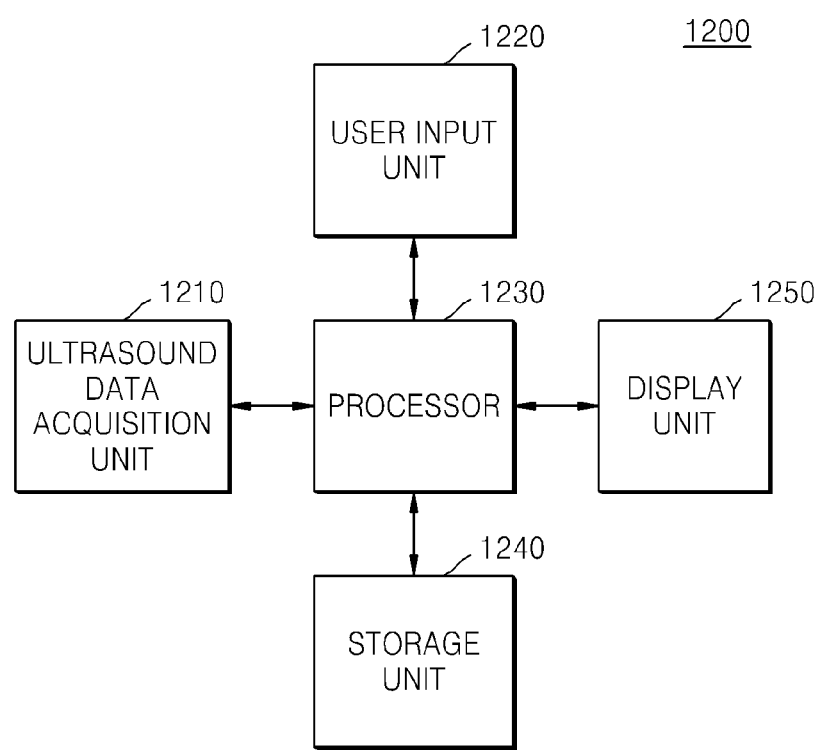
FIG. 12 is a block diagram showing a configuration of an ultrasound system according to another exemplary embodiment of the present invention.

FIG. 12 is a block diagram showing a configuration of an ultrasound system 1200 according to another exemplary embodiment of the present invention. Referring to FIG. 12, the ultrasound system 1200 according to the present embodiment includes an ultrasound data acquisition unit 1210, a user input unit 1220, a processor 1230, a storage unit 1240, and a display unit 1250.

The ultrasound data acquisition unit 1210 acquires ultrasound data corresponding to an ultrasound image of a living body. Since the ultrasound data acquisition unit 1210 has substantially the same function and construction as the ultrasound data acquisition unit 110, a detailed description thereof is omitted here.

The user input unit 1220 receives user input information. In the present embodiment, the input information includes first input information needed for setting an ROI corresponding to a 3D caliper. In other words, the first input information contains 2D coordinates of the ROI on 3D ultrasound image that is displayed on the display unit 150. The input information also includes second input information needed for selecting at least one of a plurality of objects within a living body. The input information further includes third input information needed for setting a reference value that will be used to determine a position of a 3D caliper (i.e., an ROI) with respect to a 3D ultrasound image in a depth direction. The input information further includes fourth input information needed for changing a 3D position of a virtual plane VP. That is, the fourth input information includes at least one of information needed for rotating the virtual plane VP and information needed for moving the virtual plane VP. However, the input information is not limited thereto. The user input unit 1220 includes a control panel, a track ball, a touch screen, a keyboard, and a mouse.

The processor 1230 is connected to the ultrasound data acquisition unit 1210 and the user input unit 1220. The processor 1230 includes a CPU, a microprocessor, and a GPU.

Figure 13:
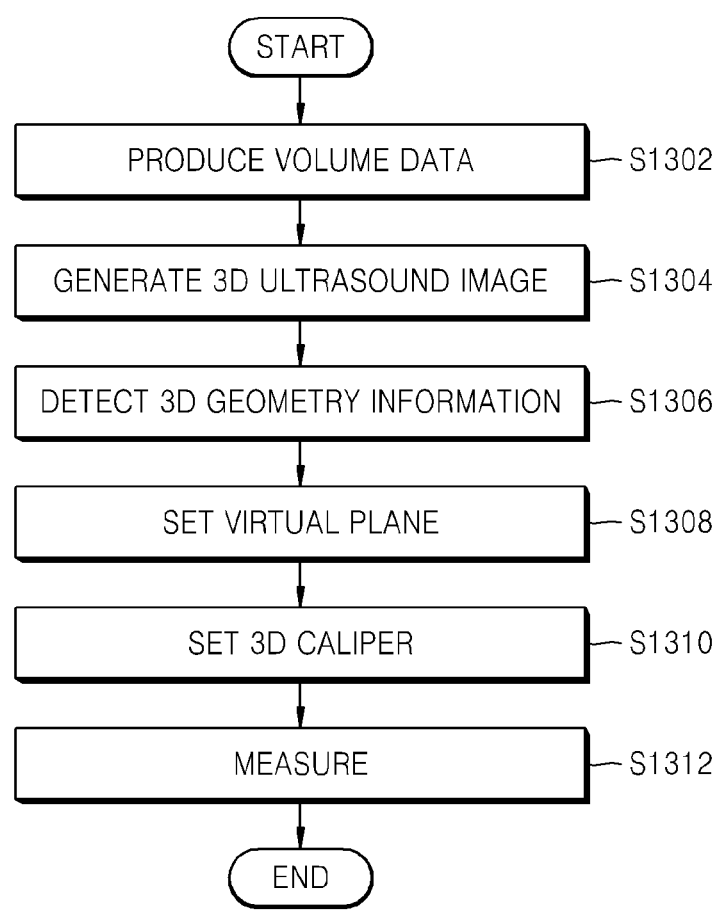
FIG. 13 is a flowchart of a method of creating measurement information by setting a 3D caliper according to another exemplary embodiment of the present invention.

FIG. 13 is a flowchart of a method of creating measurement information by setting a 3D caliper according to another exemplary embodiment of the present invention. Referring to FIGS. 12 and 13, the processor 1230 produces volume data VD as shown in FIG. 5 by using ultrasound data provided by the ultrasound data acquisition unit 1210 (S1302).

The processor 1230 performs volume rendering on the volume data VD to generate a 3D ultrasound image (S1304). In the present embodiment, the volume rendering includes perspective rendering, but is not limited thereto.

The processor 1230 then detects 3D geometry information (i.e., 3D coordinates) of an ROI from the volume data VD (i.e., 3D ultrasound image) based on input information provided by the user input unit 1220 (S1306).

Figure 14:
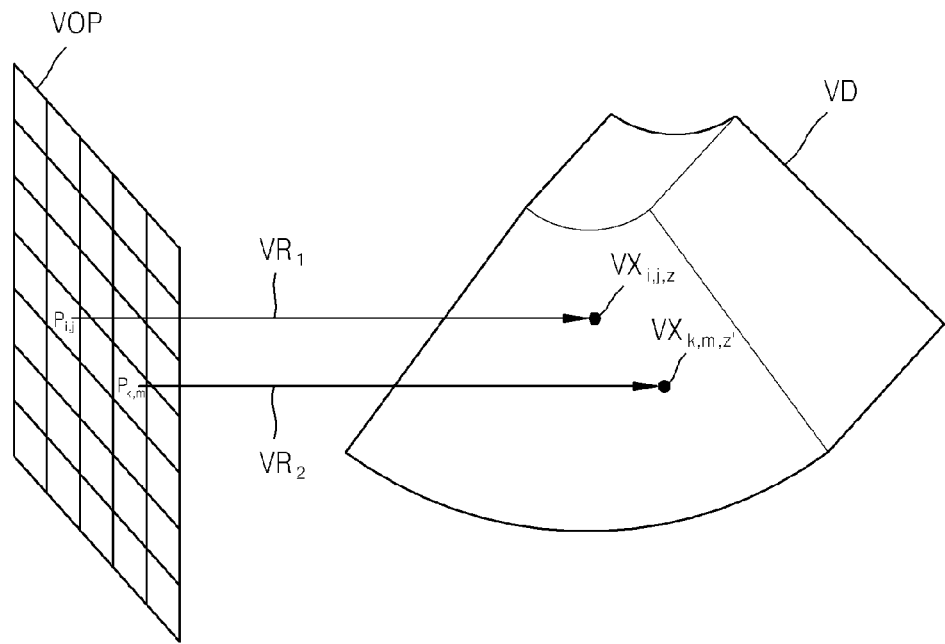
FIG. 14 is a diagram illustrating an observation plane, an ROI, a virtual ray, and a voxel according to another exemplary embodiment of the present invention.

In one embodiment, the processor 1230 may set a reference value corresponding to an object according to a reference value preset for the object, based on input information (i.e., second input information) provided by the user input unit 1220. The preset reference value may be stored in the storage unit 1240. As shown in FIG. 14, the processor 1230 sets a virtual observation plane VOP consisting of a plurality of pixels based on the volume data VD. The processor 1230 detects pixels corresponding to an ROI (i.e., points) from the virtual observation plane VOP based on input information (i.e., first input information) provided by the user input unit 1220. That is, as shown in FIG. 14, the processor 1230 detects pixels $P_{i,j}$ and $P_{k,m}$ corresponding to the ROI based on 2D position information (i.e., 2D coordinates) of the ROI. The processor 1230 then projects virtual rays $VR_1$ and $VR_2$ from the detected pixels $P_{i,j}$ and $P_{k,m}$ onto the volume data VD. The processor 1230 also samples the virtual rays $VR_1$ and $VR_2$ at preset sampling intervals and acquires sampling points and sampling values at the sampling points. The processor 1230 then detects a voxel corresponding to the reference value from the volume data VD based on the sampling value. In one embodiment, the processor 1230 may cumulatively add sampling values along the propagation direction of the virtual rays $VR_1$ and $VR_2$ and detect a first voxel where a cumulative sum of the sampling values is greater than or equal to the reference value as the voxel corresponding to the reference value. In another embodiment, the processor 1230 may compare a sampling value with a preset threshold value, detect sampling values that are greater than or equal to the preset threshold value, cumulatively add the detected sampling values along the propagation direction of the virtual rays $VR_1$ and $VR_2$, and detect a first voxel where a cumulative sum of the sampling values is greater than or equal to the reference value as the voxel corresponding to the reference value. In yet another embodiment, the processor 1230 may compare a sampling value with a reference value, detect a first sampling value that is greater than or equal to the reference value, and detect voxels $VX_{i,j,z}$ and $VX_{k,m,z'}$ corresponding to the first sampling value as the voxels corresponding to the reference value. The processor 1230 then sets 3D geometry information (i.e., 3D coordinates) of the detected voxels $VX_{i,j,z}$ and $VX_{k,m,z'}$ as 3D geometry information (i.e., 3D coordinates) of an ROI.

In still another embodiment, the processor 1230 sets a reference value corresponding to the object based on input information (i.e., second input information and third input information) provided by the user input unit 1220, and detects 3D geometry information (3D coordinates) of an ROI based on the set reference value, as describe above.

Figure 15:
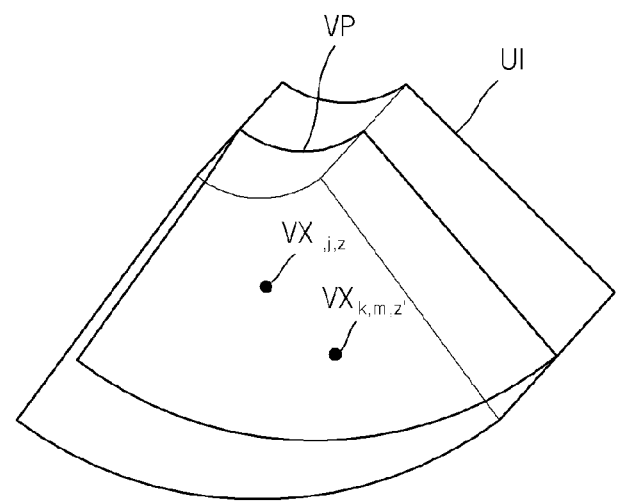
FIG. 15 is a diagram illustrating a 3D ultrasound image and a virtual plane according to another exemplary embodiment of the present invention.

The processor 1230 sets a virtual plane on the 3D ultrasound image based on the detected 3D geometry information (i.e., 3D coordinates) (S1308). In the present embodiment, as shown in FIG. 15, the processor 1230 sets a virtual plane VP corresponding to the ROI, which passes through the voxels $VX_{i,j,z}$ and $VX_{k,m,z'}$, on a 3D ultrasound image UI based on the 3D geometry information (i.e., 3D coordinates).

The processor 1230 sets a 3D caliper on the virtual plane based on the 3D geometry information (i.e., 3D coordinates) of the ROI (S1310). In detail, the processor 1230 sets a virtual plane VP on the 3D ultrasound image, and sets a 2D caliper having depth information in a depth direction of the 3D ultrasound image on the virtual plane VP as a 3D caliper, based on the detected 3D geometry information (i.e., 3D coordinates) of the ROI.

The processor 1230 then performs measurement based on the set 3D caliper to create measurement information (S1312). That is, the processor 1230 measures a length of the object by using the 2D caliper to create length information as well as measurement information including the length information and the depth information.

The processor 1230 may selectively create an ultrasound image (i.e., cross-sectional image) corresponding to the virtual plane by using the volume data VD, set an ROI on the cross-sectional image, and perform measurement based on the set ROI to create measurement information.

Referring back to FIG. 12, the storage unit 1240 stores ultrasound data acquired by the ultrasound data acquisition unit 1210 as well as input information received from the user input unit 920. In addition, the storage unit 1240 may store volume data VD created by the processor 1230 and preset reference values.

The display unit 1250 displays 3D ultrasound images and measurement information generated by the processor 1230 as well as 3D calipers. In addition, the display unit 1250 displays a cross-sectional image generated by the processor 1230.

While one or more embodiments of the present invention have been described with reference to the figures, it will be understood by those of ordinary skill in the art that various changes in form and details may be made therein without departing from the spirit and scope of the present invention as defined by the following claims.

What is claimed is:

1. A medical system comprising:
   an image data acquisition unit that acquires image data corresponding to a three-dimensional (3D) image of a living body including an object;
   a user input unit that receives first input information for setting a point; and
   a processor that generates 3D data by using the image data, generates the 3D image by using the 3D data, detects 3D geometry information corresponding to a 3D caliper from the 3D data based on the first input information, sets the 3D caliper on the 3D image based on the detected 3D geometry information, and creates measurement information,
   wherein the processor sets a virtual plane on the 3D data, sets an observation plane consisting of a plurality of pixels based on the 3D data, detects a pixel corresponding to the point from the observation plane based on the first input information, detects a voxel which is on the virtual plane and corresponds to the pixel in a predetermined direction, and sets 3D geometry information of the detected voxel as 3D geometry information of the point.

2. The medical system of claim 1, wherein the user input unit further receives second input information needed for setting the virtual plane, and
   wherein the processor sets the virtual plane based on the second input information.

3. The medical system of claim 2, wherein the user input unit further receives third input information needed for changing a 3D position of the virtual plane, and
   wherein the processor changes the 3D position of the virtual plane based on the second input information to place the virtual plane in the 3D data.

4. The medical system of claim 1, wherein the processor projects a virtual ray from the detected pixel onto the 3D data, and detects the voxel at an intersection of the virtual ray and the virtual plane.

5. The medical system of claim 4, wherein the processor sets a 2D caliper having depth information in a depth direction of the 3D image on the virtual plane as the 3D caliper, based on the 3D geometry information, measures a length of the object by using the 2D caliper to create length information, and creates measurement information including the length information and the depth information.

6. The medical system of claim 1, wherein the processor creates a cross-sectional image corresponding to the virtual plane by using the 3D data, and performs measurement based on the cross sectional image to create measurement information.

7. A method of providing measurement information, the method performed by a processor, the method comprising:
   acquiring image data corresponding to a three-dimensional (3D) image of a living body including an object;

creating 3D data by using the image data;
creating the 3D image by using the 3D data;
receiving first input information for setting a point;
detecting 3D geometry information corresponding to a 3D caliper from the 3D data based on the first input information;
setting the 3D caliper on the 3D image based on the detected 3D geometry information to create measurement information;
setting a virtual plane on the 3D data;
setting an observation plane consisting of a plurality of pixels based on the 3D data;
detecting a pixel corresponding to the point on the observation plane based on the first input information;
detecting a voxel which is on the virtual plane and corresponding to the pixel in a predetermined direction; and
setting 3D geometry information of the detected voxel as 3D geometry information of the point.

8. The method of claim 7, further comprising:
receiving second input information needed for setting the virtual plane,
wherein the step of setting the virtual plane on the 3D data comprises setting the virtual plane on the 3D data based on the second input information.

9. The method of claim 8, further comprising:
receiving third input information needed for changing a 3D position of the virtual plane, wherein the detecting of 3D geometry information corresponding to a 3D caliper from the 3D data comprises changing the 3D position of the virtual plane based on the third input information to place the virtual plane in the 3D data.

10. The method of claim 7,
wherein the step of detecting 3D geometry information comprises projecting a virtual ray from the detected pixel onto the 3D data,
and the step of detecting the voxel comprises detecting the voxel at an intersection of the virtual ray and the virtual plane.

11. The method of claim 10, wherein the setting of the 3D caliper on the 3D image based on the detected 3D geometry information to create measurement information comprises:
setting a 2D caliper having depth information in a depth direction of the 3D image on the virtual plane as the 3D caliper, based on the 3D geometry information;
measuring a length of the object by using the 2D caliper to create length information; and
creating measurement information including the length information and the depth information.

12. The method of claim 7, further comprising:
creating a cross-sectional image corresponding to the virtual plane by using the 3D data; and
performing measurement based on the cross-sectional image to create measurement information.

* * * * *